(12) United States Patent
Horbaschek

(10) Patent No.: US 6,304,627 B1
(45) Date of Patent: Oct. 16, 2001

(54) RADIOGRAPHIC DIAGNOSTIC DEVICE WITH A COMPUTED TOMOGRAPHY SYSTEM HAVING A LINE DETECTOR, AND A POSITIONABLE ADDITIONAL RADIATION DETECTOR

(75) Inventor: Heinz Horbaschek, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/557,771

(22) Filed: Apr. 25, 2000

(30) Foreign Application Priority Data

May 7, 1999 (DE) .............................. 199 21 280

(51) Int. Cl.$^7$ ........................................ A61B 6/00
(52) U.S. Cl. ............... 378/19; 378/4; 378/195; 324/318
(58) Field of Search ................... 378/4, 19, 195; 324/318

(56) References Cited

U.S. PATENT DOCUMENTS 5,525,905 * 6/1996 Mohapatra et al. ............... 324/318
5,590,655 * 1/1997 Hussman ........................... 128/653.1
5,832,056 * 11/1998 Mochitate et al. ................. 378/195

* cited by examiner

Primary Examiner—Robert H. Kim
Assistant Examiner—Pamela R. Hobden
(74) Attorney, Agent, or Firm—Schiff Hardin & Waite

(57) ABSTRACT

Radiographic diagnostic device has a projection unit that is formed as a computer tomography system with a radiation emitter and a line detector, which are constructed such that they can be rotated around a projection area opposite one another. A support apparatus with a support plate for an examination subject is provided. The radiographic diagnostic device has an additional radiation receiver allocated to it so that the additional radiation receiver can be moved from a standby position into a pick-up position for receiving a radiation beam that emanates from the radiation emitter of the computed tomography system. Both computed tomography projections and conventional X-ray projections can be obtained with the radiographic diagnostic device when the additional radiation receiver is realized as a radiographic film, a solid-state detector, or a storage foil.

9 Claims, 2 Drawing Sheets

RADIOGRAPHIC DIAGNOSTIC DEVICE WITH A COMPUTED TOMOGRAPHY SYSTEM HAVING A LINE DETECTOR, AND A POSITIONABLE ADDITIONAL RADIATION DETECTOR

BACKGROUND OF THE INVENTION

1. Field of the Invention

The present invention relates to a radiographic diagnostic device with a projection unit formed as a computed tomography system with a radiation emitter and a line detector, which can be moved jointly about a projection area, and with a support apparatus for an examination subject that has a support plate.

2. Description of the Prior Art

A radiographic diagnostic device of this type is known from U.S. Pat. No. 5,639,419, for example. In this computed tomography device, a frame, known as a gantry, is provided, which carries a rotatably mounted projection unit consisting of a radiation emitter and a line-shaped radiation detector arranged opposite one another for transirradiating an examination area under different projections. Furthermore, a support apparatus with a displaceable support plate is allocated to the computed tomography device, on which an examination subject is supported and can be moved into the examining area. To this end, the support plate is mounted such that it can be displaced at least along its longitudinal axis. In the examining area, which is formed by a central, generally circular tunnel-like opening of the gantry, a radiation examination of the subject can be conducted by actuating the projection unit to emit radiation while rotating around the examination subject, and the signals of the line-shaped radiation detector are read out. The output signals that can be derived from the line-shaped radiation detector are fed to a computer, which generates image signals from them, which can be rendered on a display device. With such a computed tomography device, cross-sectional projections of an examination subject are obtained. It is also possible to displace the support plate with the examination subject thereon in the examining area along the longitudinal axis of the support plate while emitting radiation with the projection unit remaining stationary, so that it is also possible to create survey projections. In the computing unit, the cross-sectional projections can be combined into a volume projection in known fashion, so that it is possible to display the examination area in three dimensions. Such a representation is also possible by means of a spiral scan of the examination area, wherein the support plate with the examination subject is moved, preferably continuously, along the longitudinal axis of the support plate during the rotating radiation scan. For the radiation scan of the examination subject as described above, the radiation beam emanating from the radiation emitter is limited by a diaphragm into a narrow radiation fan and is incident on the line-shaped radiation detector, which has a frontally attached radiation diaphragm.

SUMMARY OF THE INVENTION

An object of the present invention is to provide a radiographic diagnostic device of the type described above which is more versatile than conventional systems.

This object is inventively achieved in a radiographic diagnostic device with increased utility which has an additional radiation receiver which can be moved from a standby position into an image pickup position for receiving a radiation beam that emanates from the radiation emitter of the computed tomography system. In this way, it is possible to create not only the above-described computed tomography projections, but also conventional X-ray projections (radiographs) or fluorscopic images particularly when the additional radiation receiver is fashioned as a radiographic film, a solid-state detector, or a memory film, and when the radiation beam emanating from the radiation emitter of the projection unit can be shaped by a diaphragm corresponding to the projections to be made.

It is advantageous when the additional radiation receiver can be moved into a position that is parallel to the support plate or tiltable relative to it, at least in the pick-up position, so that the center ray of the radiation beam emanating from the radiation emitter of the projection unit strikes the surface of the additional radiation receiver substantially perpendicularly. Distortions are thus avoided.

When the standby position and the pick-up position are located beneath the support plate, then a compact radiographic diagnostic device is obtained.

Alternatively, the additional radiation receiver can be moved from the standby position into the pick-up position via an arm, which makes it possible to retrofit an existing computed tomography device easily without requiring significant structural measures or modifications.

DESCRIPTION OF THE PREFERRED EMBODIMENTS

Figure 1:
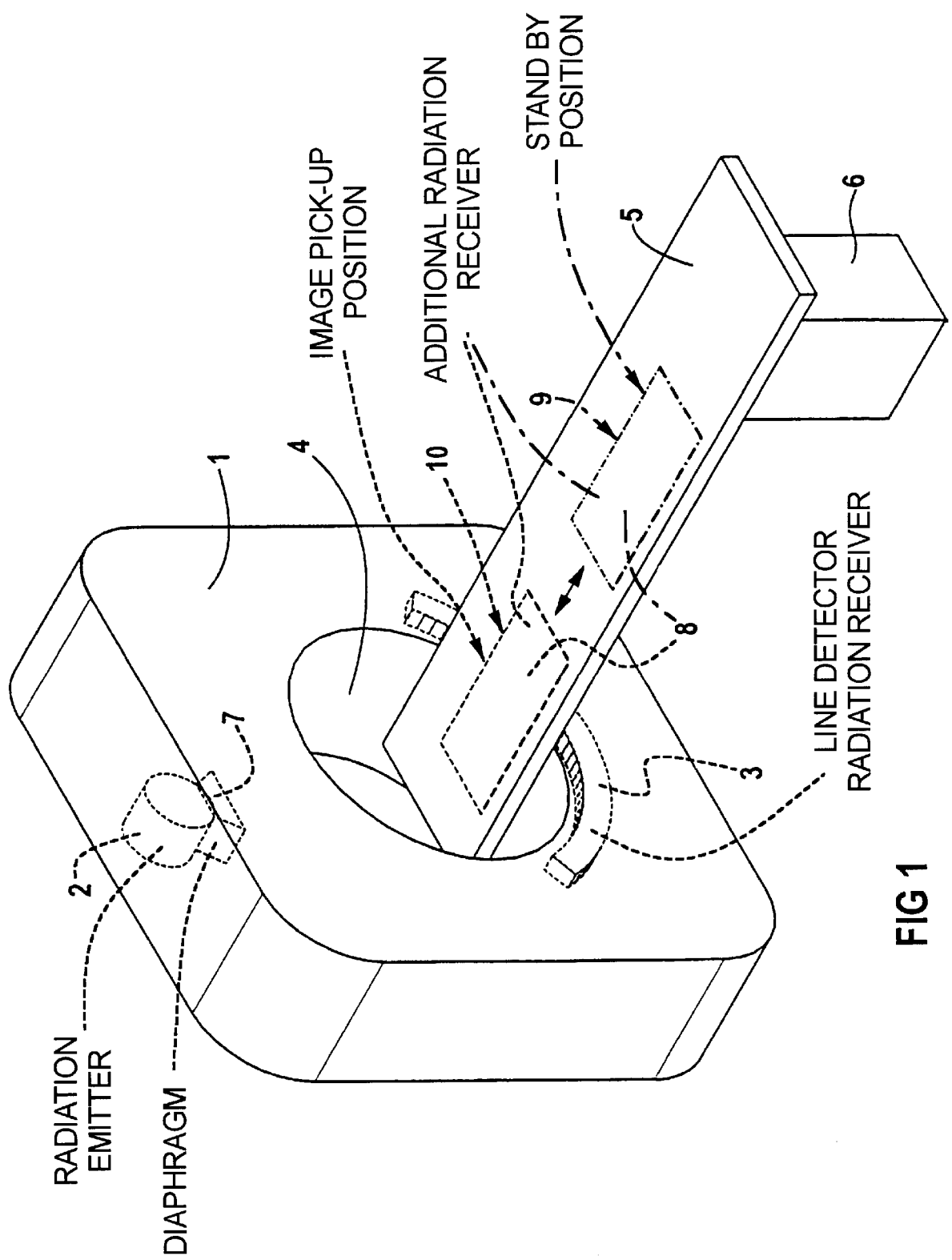
FIG. 1 SHOWS a first exemplary embodiment of a radiographic diagnostic device according to the invention.

In FIG. 1, a basic representation of an exemplary embodiment of a radiographic diagnostic device is shown having a gantry 1. A schematically, represented projection unit has a radiation emitter 2 and a line detector 3 that can be jointly displaced around a projection area 4 located in the gantry 1. The projection area 4 is formed by a tunnel-like opening into which an examination subject can be brought on a support plate 5 of a support apparatus 6. By rotating the projection unit during a radiation scan, the line detector 3 can obtain signals that can be rendered as image signals on a display device. The radiation emitter 2 has a radiation diaphragm 7 allocated to it, by which the radiation beam emanating from the emitter 2 can be gated. According to the invention, the radiographic diagnostic device has an additional radiation receiver A allocated to it, which can be constructed as a surface type radiation detector, for instance as a radiographic film, a solid-state detector, or a fluorescent storage plate or storage foil. In the exemplary embodiment represented in FIG. 1, the additional radiation receiver 8 has components allocated to it by which it can be moved from a standby position 9 into a pick-up position 10. For displacement of the additional radiation receiver 8, guide rails can be provided beneath the support plate 5, along which a fixture for the additional radiation receiver 8 can be displaced. The additional radiation receiver thus can be displaced manually or with a belt extending along the support plate 5, to which a drive system is allocated.

When creating the above mentioned computed tomography projections, the radiation beam emanating from the radiation emitter 2 must be gated to a narrow radiation fan by the radiation diaphragm 7. When, in this regard, conventional X-ray exposures or a fluoroscopy is conducted, the additional radiation receiver 8 must be moved into the pick-up position 10, and the radiation emanating from the emitter 2 must be gated into a beam by the radiation diaphragm 7 so that it is limited to the examining area. The radiation beam then is incident on the additional receiver 8 in the pick-up position 10 of the additional radiation receiver 8. Conventional radiographic projections or fluoroscopies thus can be performed using the radiation emitter 2 of a computed tomography system. A radiographic diagnostic device that is constructed in this way is thus more versatile. Since such a gantry 1 of a computed tomography device is also tiltable so as to enable oblique projections, it is advantageous when the additional radiation receiver 8 can be so oriented, at least in the pick-up position 10, so that the center ray of the radiation beam emanating from the radiation emitter 2 strikes its surface substantially perpendicularly.

The pivoting of the radiation receiver 8 can be effectuated in connection with movement of the gantry 1. Alternatively, the fixture for the additional radiation receiver 8 can be pivotable around at least one pivoting axis by mechanical or electromechanical pivoting means.

Figure 2:
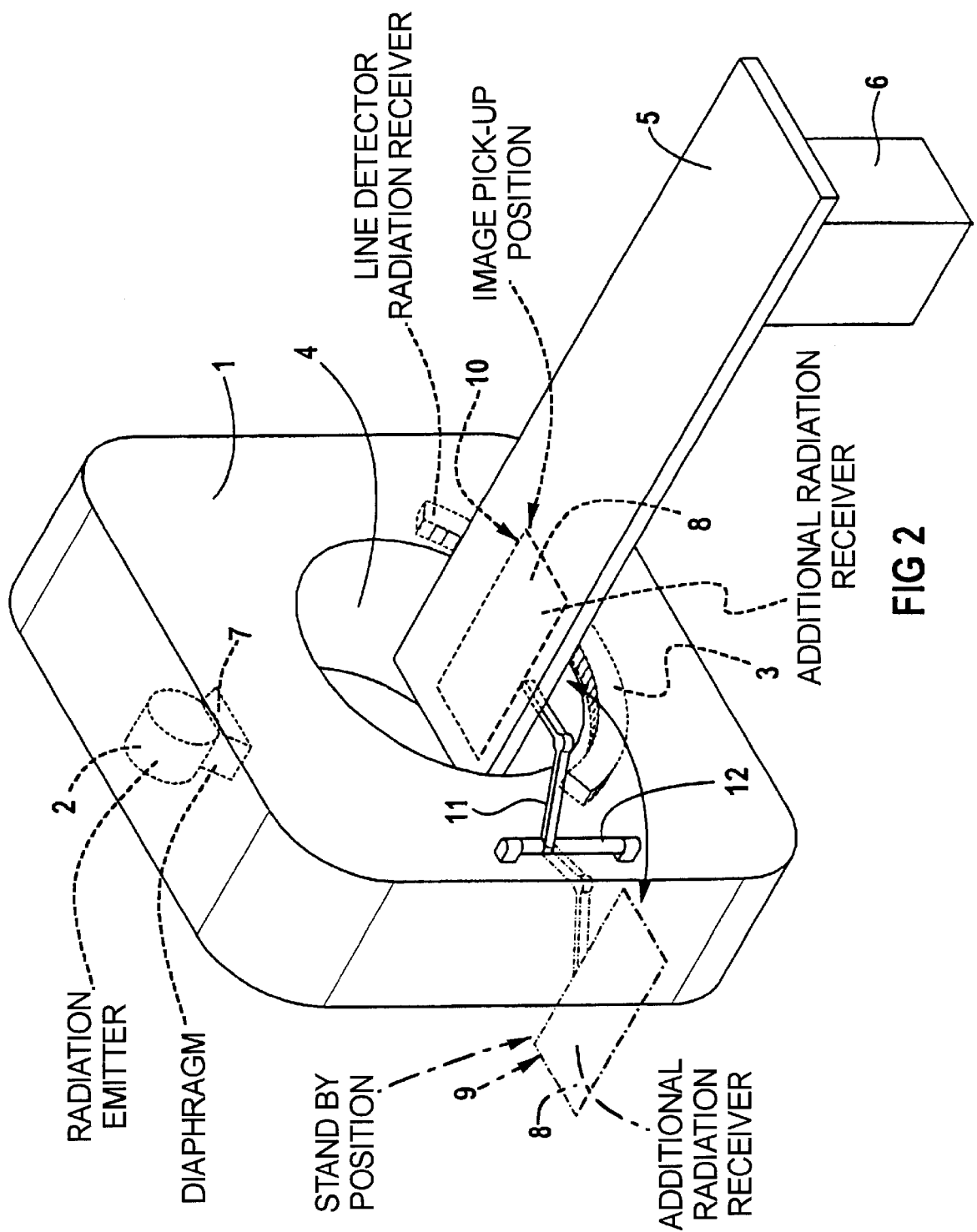
FIG. 2 shows another exemplary embodiment of a radiographic diagnostic device according to the invention.

FIG. 2 shows an exemplary embodiment of a radiographic diagnostic device according to the invention, wherein elements already described in FIG. 1 are provided with the same reference characters. Unlike the exemplary embodiment represented in FIG. 1, here an arm 11 at the gantry 1 can be pivoted around an axis 12, so that the additional radiation receiver 8 can be moved from the standby position 9 (dotted line) into the pick-up position 10. In the scope of the invention, other displacement mechanisms can be used, which are arranged on the floor or ceiling, for example a robot arm.

Although modifications and changes may be suggested by those skilled in the art, it is the intention of the inventor to embody within the patent warranted hereon all changes and modifications as reasonably and properly come within the scope of his contribution to the art.

I claim as my invention:

1. A radiographic diagnostic device comprising:
   a projection unit formed by a computed tomography system having a radiation emitter which emits a radiation beam, and a line detector radiation receiver and a gantry for rotating said radiation emitter and said line detector radiation receiver around a projection area while said radiation emitter emits said radiation beam, said radiation beam being incident on said line detector radiation receiver;
   a support apparatus for an examination subject having a support plate movable relative to said projection area; and
   an additional radiation receiver and a mount for said additional radiation receiver for selectively moving said additional radiation receiver from a standby position out of said radiation beam into an image pick-up position within said radiation beam.

2. A radiographic diagnostic device as claimed in claim 1 further comprising a radiation diaphragm connected to said radiation emitter for gating said radiation beam to form a narrow radiation fan.

3. A radiographic diagnostic device as claimed in claim 1 wherein said additional radiation receiver is selected from the group consisting of radiographic film, solid state detectors, fluorescent storage plates, and storage foils.

4. A radiographic diagnostic device as claimed in claim 1 wherein said mount for said additional radiation receiver comprises said support plate, and wherein said support plate is movable into and out of said projection area to selectively move said additional radiation receiver between said standby position and said image pick-up position.

5. A radiographic diagnostic device as claimed in claim 1 wherein said mount for said additional radiation receiver comprises a movable arm having an end to which said additional radiation receiver is attached.

6. A radiographic diagnostic device as claimed in claim 5 wherein said movable arm is a robot arm.

7. A radiographic diagnostic device as claimed in claim 5 wherein said movable arm comprises a pivoting arm.

8. A radiographic diagnostic device as claimed in claim 5 wherein said movable arm is mounted at said gantry.

9. A radiographic diagnostic device as claimed in claim 1 wherein said mount allows selective orientation of said additional radiation receiver, at least in said pick-up position, so as to be parallel to or tilted relative to said support plate.

\* \* \* \* \*